United States Patent [19]

Baldacci et al.

[11] Patent Number: 4,725,672

[45] Date of Patent: Feb. 16, 1988

[54] CONJUGATE OF 9-(2-HYDROXYETHOXYMETHYL)-GUANINE WITH LACTOSAMINATED HUMAN ALBUMIN, PROCESS FOR THE PREPARATION THEREOF AND PHARMACEUTICAL COMPOSITIONS CONTAINING IT

[75] Inventors: Massimo Baldacci, Pisa; Luigi Fiume, Bologna; Corrado Busi, Bologna; Alessandro Mattioli, Bologna, all of Italy

[73] Assignee: Laboratori Baldacci S.p.A., Pisa, Italy

[21] Appl. No.: 921,209

[22] Filed: Oct. 21, 1986

[30] Foreign Application Priority Data

Oct. 21, 1985 [IT] Italy ............................... 22559A/85

[51] Int. Cl.[4] ............................................. C07K 15/14
[52] U.S. Cl. ....................................... 530/363; 424/89;
514/8; 514/21; 530/362; 530/395; 530/397
[58] Field of Search ............... 530/362, 363, 395, 397;
514/21, 8; 424/89

[56] References Cited

PUBLICATIONS

Analytical Biochemistry, 98, 319–328 (1979), Quinn et al.
FEBS Letters, 115, No. 2, 185–188 (1980), Feix et al.
Science, 227, 1296–1303 (1985), Dolin.
FEBS Letters, 153, No. 1 (1983), Aurialitt et al.

Primary Examiner—Howard E. Schain
Attorney, Agent, or Firm—Cushman, Darby & Cushman

[57] ABSTRACT

A conjugate of 9-(2-hydroxyethoxymethyl)-guanine with lactosaminated human albumin is therapeutically more efficacious than the free drug in the treatment of chronical hepatitis induced from Virus B. For the preparation of the conjugate an aqueous solution of 9-(2-hydroxyethoxymethyl)-guanine in form of a derivative, particularly monophosphate, and an aqueous solution of lactosaminated human albumin are reacted in the presence of 1-ethyl-3-(dimethylaminopropyl)-carbodiimide, by adjusting the pH to the value of 7.5 and by maintaining the reaction mixture for 24 hours under stirring and in the dark.

6 Claims, No Drawings

CONJUGATE OF 9-(2-HYDROXYETHOXYMETHYL)-GUANINE WITH LACTOSAMINATED HUMAN ALBUMIN, PROCESS FOR THE PREPARATION THEREOF AND PHARMACEUTICAL COMPOSITIONS CONTAINING IT

The present invention relates to a novel compound, namely the conjugation product of 9-(2-hydroxyethoxymethyl)-guanine with lactosaminated human albumin, useful in the therapeutic treatment of chronical hepatitis induced from Virus B.

The 9-(2-hydroxyethomymethyl)-guanine, also known as acyclovir (ACV), having the formula:

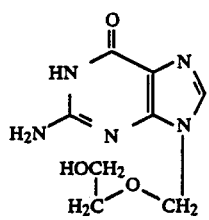

in an anti-viral drug of widespread use in the herpetic infections (Dolin L., Science 227, 1296–1303 (1985). Recently it has also been used in the treatment of chronical hepatitis induced from Virus B with good results (Weller, I. V. D. et al., Lancet i, 273, (1982), and Weller I. V. D. et al, J. Antimicr. Chem. 11, 223–231, (1983) mainly in association with interferon (Schalm S. W. et al, Lancet ii, 358) 360, 1985)). However ACV, at the dosages at which the reproduction of the virus of hepatitis B (HBV) is inhibited, (5–15 mg/kg), may cause renal lesions (Weller I. V. D. et al, J. Antimicr. Chem. 11, 223–231, (1983); Balfour H. H. Annu Rev. Med. 35, 279–291, 1984) and alterations of the central nervous system (Balfour ibidem).

It has been now found and is the object of the present invention that these problems and drawbacks are substantially and advantageously solved by means of the conjugation product of acyclovir with lactosaminated human albumin (L-SA) with a bridging bond selected among monophosphate, glutarate and succinate.

The lactosaminated human albumin is a neoglycoprotein which selectively penetrates into the hepatocytes after interaction with a receptor specific for the proteins ending with galactose present only on the parenchimal cells of liver (Wilson G., J. Biol. Chem. 253, 2070, (1978)). It has been successfully used in the mouse as the hepatotropic vehicle (carrier) of adenine arabinoside monophosphate (ARA-AMP) (Fiume L. et al, FBS Lett. 129, 261–264 (1981); Fiume L. et al. Gut 25, 1392–1398, (1984).

On the basis of the tests carried out it has been in fact found that the dose of conjugated acyclovir to be administered in order to inhibit the synthesis of viral DNA in the liver is about 6% of that of free acyclovir capable of achieving the same inhibition degree. Otherwise stated, thus, the conjugated compound according to the present invention seems to be capable of increasing the chemiotherapeutical index of ACV in the treatment of chronical hepatitis induced from virus B with a substantial reduction or elimination of the aforesaid side effects, untolerable or anyhow highly disturbing for the patient.

As already mentioned it is also an object of the present invention the process for the preparation of the conjugate comprising the use of derivative of acyclovir, selected among monosphosphate, succinate and glutarate, and the bonding of the derivative to the lactosaminated human albumin by means of carbodiimides or, as an alternative (in the case of succinate and glutarate), by means of their hydroxysuccinimidic ester, or by the method of the mixed anhydride.

According to the preferred embodiment of the process of the invention, the monophosphate derivative of acyclovir is bonded to the lactosaminated albumin by means of 1-ethyl-3-(dimethylaminopropyl)-carbodiimide (ECDI), the reaction being carried out in aqueous solution at pH higher than 6.5.

More particularly it has been found, that the desired results are obtained by operating at pH 7.5 at 25° C. and by maintaining the reaction mixture in the dark for 24 hours under stirring.

Instead of ECDI other carboddimides can be used, such as 1-cyclohexyl-3-(2-morpholinyl-(4)-ethyl-carbodiimide.

ACV monophosphate (ACV-MP) has been obtained by adding phosphorus oxychloride to a cooled suspension ($-2°$ C.) of ACV in triethylphosphate (Yoshikawa M. et al, Tetrahedon Letters 50, 5065–5068, (1967) and Le Page G. A. et al, Cancer Res. 35, 3036–3040, 1975)).

It has been purified by chromatography through a column of DOWEX-1 formiate eluted with a continuous gradient of formic acid (0 to 4M). Lactosaminated human albumin with 30 sugar residues ($L_{30}$-HSA) has been obtained by the method of reductive amination (Schwartz B. A. et al. Arch. Biol. Chem. Biophys. 181, 542–549, (1977)).

ACV-MP has been conjugated with $L_{30}$-HSA by the following process: 1 g (3.27 mmoles) of ACV-MP and 1 g (12.6 μmoles) of $L_{30}$-HSA are dissolved in 20 ml $H_2O$. The pH is adjusted to 7.5 with 10 N NaOH and 1 g (5.21 mmoles) ECDI is added. After 24 hours incubation at 25° C., under stirring and in the dark, the reaction mixture is dialized against 0.9% NaCl to remove the unbonded ACV-MP, the ECDI and its ureic derivative. When the dializate does no longer show an absorption at 255 nm the conjugate is collected and concentrated to 500 mg/10 ml in minicon B-15 (Amicon) cells. 1 ml fractions (containing 50 mg conjugate and 9 mg NaCl) are lyophilized. At the time of use a fraction is dissolved in 1 ml $H_2O$ and, if necessary, further diluted with 0.9% NaCl.

The molar ratio ACV/$L_{30}$-HSA is determined by calculating the concentration of ACV at 255 nm ($E^{1\%}=528.6$) after having subtracted the albumin absorption at that wavelength ($E^{1\%}=3.43$). The albumin concentration is measured by the method of Lowry et al (J. Biol. Chem. 193, 265–275, 1951). The molar ratio ACV/$L_{30}$-HSA in several conjugate preparations has been found to vary between 10 and 12.

Without imposing undue limitations to the present invention, it seems plausible that the advantageous results achieved by the present invention are to be connected to the lysosomatropic approach of the anti-viral chemiotherapy (Balboni P. G. et al, Nature, 264, 181–183 (1976) and Fiume L. et al., FEBS Lett. 153, 6–10 (1983)).

The conjugation of ACP-MP with $L_{30}$-HSA does not reduce but on the contrary, for reasons presently unknown, causes the capacity of this carrier of interacting with the receptor present on the surface of hepatocytes to be increased. As a matter of fact, as shown in the following table 1, the disappearance from the mouse blood of [$^{14}$C] marked asialofetuine (AF) is inhibited by the conjugate in a significatively higher rate than an equal amount of non conjugated L$_{30}$-HSA. (Fetuine is a glycoprotein of the bovine phoetal serum which, after removal of the sialic acid, penetrates selectively into the hepatocytes, after having interacted with the receptor for the proteins ending with galactose residues).

Fetuine has been enzymatically desialated (Morell A. G. et al, J. Biol. Chem. 241 3745-3749 (1966)). Then it has been marked with [$^{14}$C] formaldehyde according to Cox. R. A. and Greenwell P., Biochem. J. 186, 861-872 (1980). Swiss female mice of 28-30 g have been administered by intravenous route with 2 μg/g of [$^{14}$C] AF (4.9×10$^6$ dpm/mg).

L$_{30}$-HSA and the conjugate have been intravenously administered at the dose of 2 μg/g simultaneously with [$^{14}$C] AF. In all cases the injected volume was 10 μl/g. After 10 minutes blood samples were taken from the retroorbital plexus of the animals under ether induced anaesthesia and the radioactivity of the plasma was measured. Each value represents the average (±standard error) of the results obtained in 5 animals. The difference between the results of animals administered with L$_{30}$-HSA and those of the animals administered with the conjugate, as evaluated by the t values of Student, is significative (P<0.02).

TABLE 1

Effect of the conjugated L$_{30}$-HSA-ACV-MP$_{10}$ on the disappearance from the mouse plasma of [$^{14}$C] AF marked asialofetuine

| Compound injected with [$^{14}$C] AF | dpm/ml of plasma |
|---|---|
| none | 3,753 ± 752 |
| L$_{30}$-HSA | 7,501 ± 145 |
| L$_{30}$-HSA-ACV-MP$_{10}$ | 8,733 ± 342 |

Table 2 shows the effect of ACV, ACV-MP and of the conjugate L$_{30}$-HSA-ACV-MP$_{10}$ on the incorporation of thymidine in the DNA of liver, intestine and medulla ossium of mice affected by hepatitis induced from Ectromelia virus. In these animals the incorporation of thymidine in the liver is caused by the synthesis of viral DNA (Fiume L. et al, FEBS Lett. 129-261-264, XX (1981)).

The lowest dose of ACV giving place in a significative inhibition of the DN synthesis in the liver was 10 μg/g corresponding to that used in patients affected by chronical hepatitis B.

At that dose ACV does also inhibit in significant rate the DNA synthesis in the intestine. ACV-MP in free form was not more active than ACV. ACV-MP conjugated with L$_{30}$-HSA on the contrary caused the inhibition of DNA synthesis in the liver at a dose of 0.6 μg/g only. Moreover no significant inhibition at the intestine and medulla ossium was induced. The experimental work has been carried out as described by Fiume L. et al, GUT 25, 1392-1398, (1984). The results (dpm/mg DNA) have been statistically evaluated by means of the t test of Student and considered either significative (S) or non significative (NS) for P <or> 0.05, respectively.

TABLE 2

Effect of AVC-MP and of the conjugate L$_{30}$-HSA-ACV-MP$_{10}$ on the incorporation of [$^3$H] thymidine in the DNA of liver, intestine, and medulla ossium of mice affected by hepatitis induced from Ectromelia virus.

| Injected Compound | administered dose of ACV (μg/g) | Time between administrations of compounds and [$^3$H] thymidine (h) | INHIBITION OF DNA SYNTHESIS (%) | | |
|---|---|---|---|---|---|
| | | | Liver | Intestine | Medulla Ossium |
| L$_{30}$-HSA | 0 | 1 | 0 | 7 | 0 |
| ACV | 5 | " | 0 | 0 | 0 |
| ACV | 10 | " | 42(S) | 38(S) | 15(NS) |
| ACV | 100 | " | 65(S) | 75(S) | 59(S) |
| ACV-MP | 5 | " | 15(NS) | 23(NS) | 20(NS) |
| L$_{30}$-HSA-ACV-MP$_{10}$ | 0.6 | " | 40(S) | 6(NS) | 0 |
| L$_{30}$-HSA-ACV-MP$_{10}$ | 1.2 | " | 55(S) | 16(NS) | 7(NS) |
| ACV | 10 | 2 | 32(NS) | 16(NS) | 5(NS) |
| L$_{30}$-HSA-ACV-MP$_{10}$ | 0.6 | " | 28(NS) | 0 | 0 |

These observed data indicate that, after administration of the conjugate, ACV is concentrated in the liver wherein it is released in a pharmacologically active form. It seems thus experimentally demonstrated that the conjugate of ACV-MP with lactosaminated human albumin may cause the therapeutical index of ACV to be increased in the treatment of chronical hepatitis B, both if administered alone and if administered in combination with interferon.

Conjugates of ACV with lactosaminated albumin can also be obtained according to processes different from that used by the Applicant. ACV may be converted, by means of glutaric anydride, to ACV-glutarate, or by means of the succinic anhydride to the ACV-succinate.

Subsequently these derivatives can be bonded to the L-SA either through their hydroxysuccinimidic ester, or through the method of the mixed anhydride or by using carbodiimides. These processes have been already used for the bonding of ACV to bovine and rabbit albumins and the human immunoglobulins (Quinn, R. P. et al. Analyt. Biochem. 98, 319-328 (1979). The resulting derivatives have been used as immunogens to obtain antibodies retaining ACV which are used for the radioimmunological dosing of this drug.

By one of these processes, another anti-viral nucleoside, viz. adenine arabinoside (Ara-A) has been converted into ara-A-glutarate which has been then bonded to the asialofetuin throught its hydroxysuccinimidic ester. A conjugate ara-A-glut-AF has been obtained which demonstrated to be pharmacologically active in inducing in the mouse a hepatic targeting of ara-A (Fiume et al., FEBS Lett. 116, 185-188 (1980)).

We claim:

1. Conjugate of 9-(2-hydroxyethoxymethyl)-guanine with lactosaminated human albumin by means of a bridging bond selected among monophosphate, succinate and glutarate.

2. Conjugate according to claim 1, characterized in that the molar ratio between 9-(2-hydroxyethoxymethyl)-guanine and lactosaminated albumin is of between 10 and 12.

3. A process for the preparation of the conjugate according to claim 1, characterized in that aqueous solutions of a derivative of 9-(2-hydroxyethoxymethyl)-guanine and of lactosaminated human albumin are reacted under stirring and in the dark wherein said derivative is selected among monophasphate, glutrate and succinate.

4. A process according to claim 3, characterized in that said derivative of 9-(2-hydroxyethoxymethyl)-guanine is the monophosphate and the reaction with lactosaminated human albumin is carried out in the presence of 1-ethyl-3-(diethylaminopropyl)-carbodiimide at pH higher than 6.5, at 25° C., in the dark and under stirring, for 24 hours.

5. Pharmaceutical composition, characterized by containing, as the active ingredient, the conjugate product of claims 1 or 2 in combination with the usual excipients and vehicles.

6. Pharmaceutical composition according to claim 5, useful for the therapy of chronical hepatitis induced from Virus B.

* * * * *